United States Patent [19]

Jiang et al.

[11] Patent Number: 5,216,014

[45] Date of Patent: Jun. 1, 1993

[54] FURO-COUMARINSULFONAMIDES AS PROTEIN KINASE C INHIBITORS

[75] Inventors: Jack B. Jiang, Chapel Hill; Mary G. Johnson, Durham, both of N.C.

[73] Assignee: Sphinx Pharmaceuticals Corporation, Durham, S.C.

[21] Appl. No.: 757,664

[22] Filed: Sep. 10, 1991

[51] Int. Cl.$^5$ .................... A61K 31/37; C07D 493/02
[52] U.S. Cl. ..................... 514/455; 549/282
[58] Field of Search .......... 549/282; 514/455

[56] References Cited

U.S. PATENT DOCUMENTS

| | | | |
|---|---|---|---|
| 4,260,630 | 4/1981 | Bisagni et al. | 424/283 |
| 4,816,450 | 3/1989 | Bell et al. | 514/25 |
| 5,023,270 | 6/1991 | Goupil | 514/455 |
| 5,036,102 | 6/1991 | Bachynsky et al. | 514/455 |

FOREIGN PATENT DOCUMENTS

| | | |
|---|---|---|
| 3827974 | 8/1988 | Fed. Rep. of Germany . |
| 3928900A1 | 8/1989 | Fed. Rep. of Germany . |

OTHER PUBLICATIONS

Castagna et al., Biol. Chem., 257:7847 (1982).
Grunicke et al., Adv. Enzyme Regul., 28:201 (1989).
Tritton et al., J.A. Cancer Cells, 2:95–102 (1990).
Schachtele et al., Biochem. Biophys. Res. Commun., 151:545 (1988).
Hannun et al., J. Biol. Chem., 262:13620 (1987).
Yamada et al., Biochem. Pharmacol., 37:1161 (1988).
McIntyre et al., J. Biol. Chem., 262:15730 (1987).
Lambeth et al., J. Biol. Chem., 263:3818 (1988).
Pittet et al., J. Biol. Chem., 262:10072 (1987).
Gaudry et al., Immunology, 63:715 (1988).
Wilson et al., J. Biol. Chem., 261:12616 (1986).
Fujita et al., Biochem. Pharmacol., 35:4555 (1986).
Berkow et al., J. Leukoc. Biol. 41:411 (1987).
Salzer et al., Biochem. Biophys. Res. Commun., 148:747 (1987).
Kramer et al., J. Biol. Chem., 262:5876 (1989).
Dewald et al., Biochem. J., 264:879 (1979).
Brokke et al., J. Org. Chem., 24:523 (1959).
Anderson et al., Ann. Rev. Pharmacol., Toxicol., 20:235 (1980).

*Primary Examiner*—C. Warren Ivy
*Assistant Examiner*—Ba K. Trinh
*Attorney, Agent, or Firm*—Woodcock Washburn Kurtz Mackiewicz & Norris

[57] ABSTRACT

The present invention provides novel furocoumarin-sufonamide derivatives having the formula

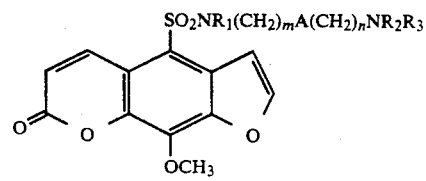

wherein $R_1$, $R_3$, $R_4$, $R_5$ and $R_6$ are independently H or lower alkyl; m, n and p are independently 2, 3, 4, 5 or 6; A is $NR_4(CH_2)_pNR_5$, $NR_6$, O or S; $R_2$ is independently H, lower alkyl or a moiety of the formula

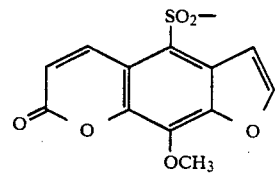

useful for inhibiting protein kinase C and treating conditions related to, or affected by inhibition of protein kinase C, particularly cancer tumors, inflammatory disease, reperfusion injury, and cardiac dysfunctions related to reperfusion injury.

6 Claims, No Drawings

FURO-COUMARINSULFONAMIDES AS PROTEIN KINASE C INHIBITORS

FIELD OF THE INVENTION

The present invention relates to diagnosis and treatment for inflammatory, cardiovascular and neoplastic diseases. More particularly, the present invention relates to novel furo-coumarinsulfonamide compounds for inhibiting activity of the enzyme protein kinase C.

BACKGROUND OF THE INVENTION

Protein kinase C (PKC) is a family of calcium stimulant and phospholipid-dependent serine/threonine -specific protein kinases which play an important role in cellular growth control, regulation, and differentiation. Protein kinase C is also fundamental to the processes involved in tumorigenicity, since it is the major high-affinity receptor for several classes tumor promoters as well as for endogenous cellular diacylglycerols. These tumor promoters also stimulate protein kinase C catalysis. Castagna et al., *Biol. Chem.* 257: 7847, 1982, reported direct activation of protein kinase C by tumor promoting phorbol esters. The mechanisms of protein kinase C action have been described in U.S. Pat. No. 4,816,450 issued Mar. 28, 1989 to Bell et al., the disclosure of which is incorporated as fully set forth herein. Protein kinase C is activated by diacylglycerol (DAG), a neutral lipid, and when activated will transfer the γ-phosphate of MgATP to a serine or threonine residue on a substrate protein.

Since the activation of protein kinase C has been implicated in several human disease processes, including cancer tumors, inflammation, and reperfusion injury, inhibition of protein kinase C activity should be of great therapeutic value in treating these conditions.

Certain protein kinase C inhibitors have been reported to potentiate the antitumor activity of cis-platin both in vitro and in vivo. See Grunicke et al., *Adv. Enzyme Regul.* 28: 201, 1989 and German Offenlegungsschrift DE 3827974. In addition, it has been suggested that protein kinase C would be a potential target for therapeutic design because of its central role in cell growth. See Tritton, T. R. and Hickman, J. A. *Cancer Cells* 2: 95-102, 1990.

Further, inflammation and reperfusion injury, particularly pertaining to cardiac injury, are common conditions for which there exists no definitive treatment despite extensive research, and appropriate treatments for these conditions are needed.

Certain protein kinase C inhibitors have been demonstrated to block platelet aggregation and release of neutrophil activating agents such as platelet activating factor, PAF. See Schachtele et al., *Biochem. Biophy. Res. Commun.* 151: 542, 1988; Hannun et al., *J. Biol. Chem.* 266: 13620, 1987; Yamada et al., *Biochem. Pharmacol.* 37: 1161, 1988. Ceratin protein kinase C inhibitors have also been shown to inhibit neutrophil activation, and chemotactic migration. See McIntyre et al., *J. Biol Chem.* 262: 15730, 1987; Lambreth et al., *J. Biol. Chem.* 263: 3818, 1988; Pittet et al., *J. Biol. Chem.* 262: 10072, 1987; and Gaudry et al., *Immunology* 63: 715, 1988. Further, certain protein kinase C inhibitors have also been shown to inhibit neutrophil degranulation and release of proteolytic enzymes and reactive oxygen intermediates. See Wilson et al., *J. Biol. Chem.* : 12616, 1986; Fujita et al., *Biochem. Pharmacol.* 35: 4555, 1986; Berkow et al., *J. Leukoc., Biol.* 41: 441, 1987; Salzer et al., *Biochem. Biophys. Res. Commun.* 148: 747, 1987; Kramer et al., *J. Biol. Chem.* 262: 5876, 1989; and Dewald et al., *Biochem. J.* : 879, 1989. It is apparent that inhibitors of protein kinase C activity have the capability of blocking all three of the most significant mechanisms of pathogenesis associated with myocardial reperfusion injury, and should thus have a decided therapeutic advantage. Additionally, the inhibitory effect of protein kinase C inhibitors on keratinocytes, and on the oxidative burst in neutrophils will lead to an anti-inflammatory effect.

German Offenlegungsschrift DE 3827974 A1 discloses therapeutic preparations comprising a protein kinase C inhibitor in combination with a lipid, a lipid analogue, a cytostatic agent or phospholipase inhibitor useful for cancer therapy. However, none of the protein kinase C inhibitors disclosed in this publication is a furo-coumarinsulfonamide derivative.

Psoralen, a furo-coumarin, has been used for many years as an antipsoriatic agent in conjunction with light treatment. See Brokke and Christensen, *J. Org. Chem.* 24: 523, 1959; Anderson and Voorhees, *Ann. Rev. Pharmacol. Toxicol.* 20: 235, 1980. Additionally, modified oligonucleotides containing a psoralen moiety have been disclosed as antiviral agents. See Weickmann, et al., Offenlegungsschrift DE 3928900A1.

SUMMARY OF THE INVENTION

The present invention provides novel furocoumarin-sulfonamides having the formula

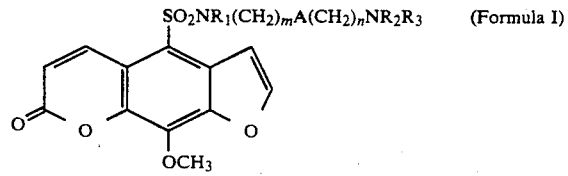 (Formula I)

wherein $R_1$, $R_3$, $R_4$, $R_5$ and $R_6$ are independently H or lower alkyl; m, n and p are independently 2, 3, 4, 5 or 6; A is $NR_4(CH_2)_pNR_5$, $NR_6$, O or S; $R_2$ is independently H, lower alkyl or a moiety of the formula

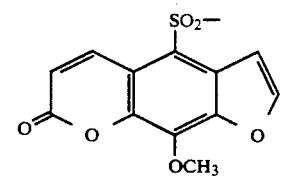

The compounds of the invention are useful for inhibiting protein kinase C and are further useful for treating conditions related to or affected by inhibition of protein kinase C activity, particularly cancer tumors, inflammatory disease, reperfusion injury, and cardiac dysfunctions related to reperfusion injury. Inhibition of protein kinase C can lead to inhibition of growth of cells and can thereby produce an anti-tumor effect. Further inhibition of protein kinase C can also lead to inhibition of the oxidative burst in neutrophils, platelet aggregation, and keritinocyte proliferation, whereby an anti-inflammatory effect is achieved. The inhibitory activities of the compounds of the invention against platelet aggregation, neutrophil activation and neutrophil release demonstrate their usefulness in treating reperfusion injury, particularly myocardial reperfusion injury.

Pharmaceutical compositions comprising a compound of the invention and a pharmaceutically acceptable carrier or diluent are also provided.

This invention is more particularly pointed out in the appended claims and is described in its preferred embodiments in the following description.

DETAILED DESCRIPTION OF THE INVENTION

The present invention provides novel furocoumarin-sulfonamides having the formula

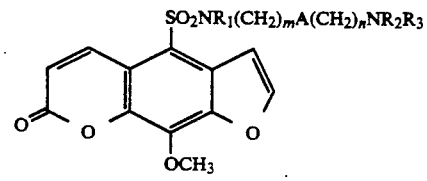

wherein $R_1$, $R_3$, $R_4$, $R_5$ and $R_6$ are preferably independently H or lower alkyl, more preferably independently H or methyl; m, n and p are preferably independently 2, 3, 4, 5 or 6, more preferably independently 3 or 4; A is preferably $NR_4(CH_2)_pNR_5$, $NR_6$, O or S, more preferably independently $NR_4(CH_2)_pNR_5$ or $NR_6$; and $R_2$ is preferably independently H, lower alkyl or a moiety of the formula

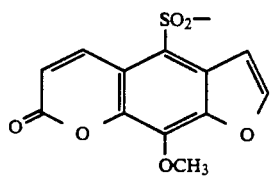

; more preferably a moiety of the formula

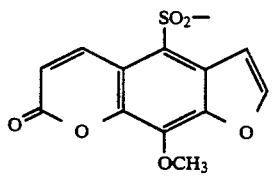

As used herein, the term lower alkyl is intended to mean $C_1$–$C_6$ alkyl. As used herein alkyl substituents include straight chain, branched and cyclic moieties, preferably straight chain species.

The compounds of the invention are useful for treating conditions related to, or affected by inhibition of protein kinase C activity, particularly cancer tumors, inflammatory disease, reperfusion injury, and cardiac dysfunctions related to reperfusion injury. Accordingly, another aspect of the invention provides methods and pharmaceutical compositions for inhibiting protein kinase C activity. The pharmaceutical compositions of the invention comprise a furo-coumarinsufonamide compounds of the invention and a pharmaceutically acceptable carrier or diluent.

The compounds of the invention are selective for protein kinase C, and have no effect on cAMP dependent protein kinase. The compounds of the invention inhibited protein kinase C in concentrations lower than those which were effective to inhibit protein kinase. Thus, the compounds of the invention should have minimal or no effect on the metabolic pathways associated with stimulation of protein kinase by cAMP.

The present invention also provides methods of inhibiting an oxidative burst in neutrophils which comprise contacting a neutrophil with a protein kinase C inhibitory amount of a furo-coumarinsufonamide compound of the invention, or contacting a neutrophil with an amount of a compound of the invention effective to inhibit such oxidative burst.

The invention further provides methods for treating inflammation which comprise administering to a mammal suffering from inflammation a protein kinase C inhibitory amount of a furo-coumarinsulfonamide of the invention, or administering to the mammal an amount of a compound of the invention effective to inhibit inflammation.

The present invention additionally provides methods for inhibiting growth of mammalian tumor cells which comprises contacting a mammalian tumor cell with a protein kinase C inhibitory amount of a furo-coumarin-sulfonamide compound of the invention, or contacting the tumor cell with an amount of a compound of the invention effective to inhibit growth of the tumor cell.

The invention thus also provides methods of treating a mammalian tumor which comprises contacting a mammalian tumor with a protein kinase C inhibitory amount of a furo-coumarinsulfonamide compound of the invention, or contacting the tumor with an amount of a compound of the invention effective to inhibit growth of the tumor.

Another embodiment of the invention provides methods of inhibiting mammalian keratinocyte proliferation which comprises administering to a mammalian keratinocyte a protein kinase C inhibitory amount of a furo-coumarinsulfonamide compound of the invention, or administering to the keratinocyte an amount of a compound of the invention effective to inhibit proliferation of the keratinocyte.

Cancer is a disease characterized in part by uncontrolled cell growth. Protein kinase C is directly involved in cellular growth control and is believed to be involved in tumor formation. Protein kinase C is the major, if not exclusive, intracellular receptor of phorbol esters which are very potent tumor promoters. Phorbol esters and other tumor promoters bind to and activate protein kinase C. Since diacylglycerol (DAG) and phorbol esters interact at the same site, DAGs have been suggested to be the "endogenous phorbol esters" by analogy with the opiate receptor where the conservation of a high affinity receptor implied the existence of an endogenous analogue. DAG has been shown to increase the affinity of protein kinase C for $Ca^{+2}$ and phospholipid and thus activates protein kinase C at cellular levels of these essential cofactors.

Extracellular signals including hormones, growth factors, and neurotransmitters are known to stimulate phosphatidylinositol turnover resulting in the generation of $IP_3$ and DAG. Structures of 40 distinct oncogenes of viral and cellular origin have revealed that oncogenes encode altered forms of normal cellular proteins. Several of the gene products appear related to growth factors or other elements involved in transmembrane signalling. These oncogene products appear to function by altering the level of critical second messengers. Cells transformed with the oncogenes ras, sis, erbB, abl, and scr have been shown to contain elevated levels of DAG which is then believed to activate protein kinase C. Indeed, studies on ras transformed cells have shown protein kinase C activation to be concomitant with elevation of DAG.

Phorbol esters, such as phorbol myristate acetate (PMA), have complex effects on cells including effects on membrane function, mitogenesis, differentiation, and gene expression. Synthetic diacylglycerols mimic many of the effects of PMA in vitro and inhibitors of protein kinase C have been shown to block PMA-induced effects on cells. Thus, protein kinase C may mediate the actions of certain oncogenes, such as ras, which cause intracellular increases in DAG and concomitant increases in protein kinase C. In addition, activation of protein kinase C leads to the expression of c-myc, c-fos, c-cis, c-fms, nuclear protooncogenes important in cell transformation. Overexpression of protein kinase C in NIH 3T3 cells causes altered growth regulation and enhanced tumorigenicity and in rat fibroblasts leads to anchorage-independent growth in soft agar. Further, overexpression of protein kinase C in these cells resulted in tumor formation in animals receiving transplanted cells.

Several studies have shown increased expression of protein kinase C in certain tumor types such as breast and lung carcinomas. Activated protein kinase C has also been detected in human colon carcinomas although increased expression on the gene level was not seen. Topoisomerases are directly modulated by protein kinase C as substrates for the enzyme and protein kinase C inhibitors have been shown to potentiate the action of chemotherapy drugs such as cis-platin. Other and more potent compounds which have been identified specifically as inhibitors of protein kinase C have shown early promise as therapeutic agents in inhibiting tumor growth in animal models.

Animal studies have shown that perhaps 50% or more of ischemic-related myocardial damage can be attributed to polymorphonuclear leukocytes (neutrophils) which accumulate at the site of occlusion. Damage from the accumulated neutrophils may be due to the release of proteolytic enzymes from the activated neutrophils or the release of reactive oxygen intermediates (ROI). Much of the "no reflow" phenomenon associated with myocardial ischemia is attributed to myocardial capillary plugging. The plugging of capillaries has been attributed to both aggregated platelets and aggregated neutrophils. Although both cell types are aggregated during the ischemic event, the relative contribution of each to capillary plugging has not yet been established. It is accepted that the damage by neutrophils to myocardial tissue proceeds through a cascade of events, one of the earliest being the bonding of activated neutrophils to damaged vascular endothelium. However, the binding of the neutrophils is significantly enhanced by their activation and this an even earlier event is the generation of molecules (such as cytokines, and chemotactic factors) which can function as activation stimuli. These molecules probably originate from damaged and aggregated platelets, from damaged vascular endothelium, or from the oxidation of plasma proteins or lipids by endothelial-derived oxidants.

Strategies for overcoming the deleterious effects of reactive oxygen intermediates have centered on the development of scavengers for the molecules. Superoxide dismutase (SOD) has been shown to be a particularly effective scavenger of superoxide, but suffers from a very short half-life in the blood. Several companies have tackled this problem by creating versions of this enzyme with increased half-lives by techniques such as liposome encapsulation or polyethylene glycol conjugation. Reports on the effectiveness of these new versions are mixed. Catalase, a scavenger of hydrogen peroxide, and hydroxyl radical scavenger has also been tested and found to be effective to varying degrees. However, none of the strategies designed to scavenge reactive oxygen intermediates will prevent the aggregation of platelets, the release of chemotactic molecules, the activation and adherence of neutrophils to vascular endothelium, or the release of proteolytic enzymes from activated neutrophils.

One advantage of protein kinase C inhibitors as therapeutics for reperfusion injury is that they have been demonstrated to i) block platelet aggregation and release of neutrophil activating agents such as PAF, 2) block neutrophil activation, chemotactic migration, and adherence to activated or damaged endothelium, and 3) block neutrophil release of proteolytic enzymes and reactive oxygen intermediates. Thus these agents have the capability of blocking all three of the most significant mechanisms of pathogenesis associated with reperfusion injury and should thus have a decided therapeutic advantage.

The novel furo-coumarinsufonamide compounds of the invention may be prepared according to scheme I or any other method known in the art. According to scheme I shown below, the starting material 8-methoxypsoralen (II) is sulfonylated to produce the corresponding sulfonyl chloride (III). The sulfonyl chloride (III) is then reacted with an appropriate polyamine (IV) to produce a compound of the invention having formula I.

Scheme I

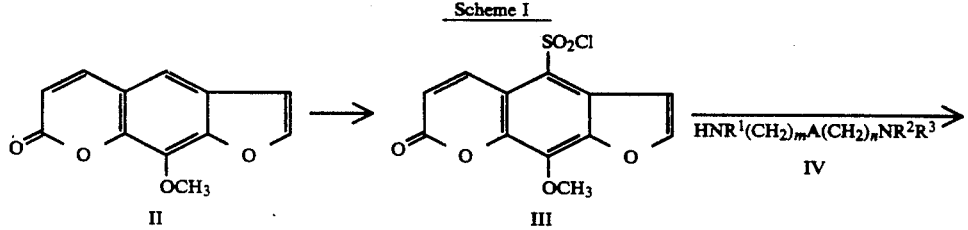

-continued
Scheme I

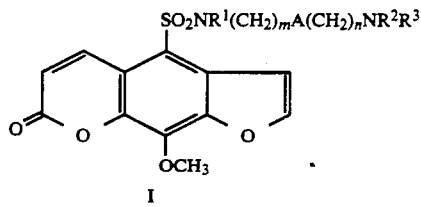

I

As used herein, a furo-coumarinsulfonamide structure has the conventional ring numbering as illustrated for coumarin in the Merck Index, Tenth Edition, Merck & Co., Inc. Rahway, N.J., 1983, p.367.

Pharmaceutically acceptable salts of the compounds of the invention are also within the scope of the invention. Such pharmaceutically acceptable salts useful in the invention include salts of hydrochloric, lactic, succinic, fumaric, malic, oxalic, methanosulfonic, sulfonic or acetic acids.

The compounds of the invention may be administered by any method that produces contact of the active ingredient with the agent's site of action in the body of a mammal, or in the body fluid or tissue including but not limited to oral, topical, hypodermal, intramuscular, intravenous, and intraparenteral administration. The compounds may be administered singly, or in combination with other compounds of the invention, other pharmaceutical compounds, such as chemotherapeutic compounds, or in conjunction with other therapies, such as radiation treatment. The furo-coumarinsufonamide derivatives are preferably administered with a pharmaceutically acceptable carrier selected on the basis of the selected route of administration and standard pharmaceutical practice.

The compounds of the invention are administered to mammals, preferably humans, in therapeutically effective amounts which are effective to inhibit protein kinase C activity, or to inhibit tumor cell growth, inhibit inflammation of tissue, inhibit keratinocyte proliferation, inhibit oxidative burst from neutrophils or inhibit platelet aggregation. The dosage administered in any particular instance will depend upon factors such as the pharmacodynamic characteristics of the particular compound of the invention, its mode and route of administration; age, health, and weight of the recipient; the nature and extent of symptoms; the kind of concurrent treatment, the frequency of treatment, and the effect desired. It is contemplated that the daily dosage of the compounds will be in the range of from about 1 to about 100 mg per kg of body weight. The compounds of the invention may be administered in single doses or divided doses. Persons of ordinary skill will be able to determine dosage forms and amounts with only routine experimentation based upon the considerations of the invention.

The compounds of the invention may also be administered orally in solid dosage forms, such as capsules, tablets, and powders, or in liquid dosage forms, such as elixirs, syrups, and suspensions. They may also be administered parenterally in sterile liquid dosage forms or topically in a carrier. The compounds of the invention may be formulated into dosage forms according to standard practices in the field of pharmaceutical preparations. See Remington's Pharmaceutical Sciences, A. Osol, Mack Publishing Company, Easton, Pa.

For example, the compounds of the invention may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration may contain coloring and flavoring to increase patient acceptance, in addition to a pharmaceutically acceptable diluent such as water, buffer or saline solution.

For parenteral administration, the compounds of the invention may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound of the invention. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

EXAMPLES

The following are specific examples which are illustrative of the present invention and are not intended to limit the scope of the invention.

EXAMPLE 1

8-methoxy-furo[3,2-g]coumarin-5-sulfonyl chloride

To 1 g (4.62 mmole) of 8-methoxypsoralen, neat in a 25 ml round bottom flask, was added dropwise 11.39 g (97.8 mmole) of chlorosulfonic acid . The reaction was stirred at room temperature for 10 minutes and the resulting dark solution was poured on ice. The resulting yellow-white precipitate was filtered and recrystallized from chloroform-petroleum ether to give a fluffy moss-colored solid of 8-methoxy-furo[3,2-g]coumarin-5-sulfonyl chloride. The yield of the compound was approximately 85% having a mass of approximately 1.2 g. The melting point of the compound was approximately 167°-169° C. $^1$H NMR (CDCl3) of the compound comprised peaks of approximately 6 4.45 (s, 3H, CH$_3$), 6.68 (d, J=9.6 Hz, 1H, CH), 7.54 (d, J=2.08 Hz, 1H, CH), 7.90 (d, J=2.08 Hz, 1H, CH), and 8.87 (d, J=9.6 Hz, 1H, CH). The infrared (IR) spectrum of the compound comprised peaks of approximately 1747, 1565, 1416, 1281, 1171, 1112, 851, 630, and 545 cm$^{-1}$. The calculated elemental analysis of the compound $C_{12}H_7O_6SCl$ comprised: C, 45.78; H, 2.24; S, 10.19; and Cl, 11.26.

The values observed experimentally comprised: C, 45.89; H, 2.29; S, 10.26; and Cl, 11.35.

EXAMPLE 2

Bis-[N-(3-ethyleneamino-1-propyl)
-8-methoxy-furo[3,2-g] coumarin-5-sulfonamide] (2)
and
N-[3-[4-(3-amino-1-propyl)-amino-1-butyl]-amino-1-
propyl]-s-methyl-furo[3,2-g]coumarin-5-sulfonamide
(1)

Under a nitrogen atmosphere, a solution comprising 1.0 g (3.2 mmoles) of 8-methoxy-furo[3,2-g]coumarin-5-sulfonyl chloride in 125 ml of methylene chloride was added dropwise into a solution of 0.32 g (1.6 mmole) of spermine in 25 ml of methylene chloride. After stirring for four hours, the precipitate was filtered, washed with methylene chloride and dried to yield title compound 1. The quantitative yield of this was approximately 65% at a mass of approximately 0.6 g. The compound has a melting point of approximately 278 to 280° C. $^1$H NMR spectrum of the compound in DMSO comprised peaks of approximately δ1.58 (m, 4H, $CH_2$), 1.65 (m, 4H, $CH_2$), 1.98 (m, 2H, NH), 2.50–2.97 (m, 14H, $CH_2$, NH), 4.33 (s, 3H, $CH_3$), 6.69 (d, J=10.0 Hz, 1H, ArH), 7.45 (d, J=2.2 Hz, 1H, ArH), 8.31 (d, J=2.2 Hz, 1H, ArH), and 8.85 (d, J= 10.0 Hz, 1H, ArH); The infrared (FT-IR) spectrum in KBr comprised peaks of approximately 3430, 3123, 2953, 1726, 1572, 1458, 1285, 1162, and 643 $Cm^{-1}$. Elemental analysis calculated for $C_{22}H_{32}N_4O_6S \times 2.75$ HCl Comprised: C, 45.49; H, 6.03; N, 9.65; S, 5.52; Cl, 16.78. The values determined experimentally comprised: C, 45.06; H, 6.01; N, 9.47; S, 5.36; Cl, 16.32.

The title compound 2 was isolated in 15% yield (0.2 g) by concentrating the filtrate and washing the filtered solid with methylene chloride to give a white solid, 207°–208° C., $^1$HNMR (DMSO): δ1.58 (M, 4H, $CH_2$), 1.70 (M, 4H, $CH_2$), 2.80 (S, 12H, $CH_2$), 4.43 (S, 6H, $CH_2$), 6.70 (dd, J=10.3 Hz and 1.6 Hz, 2H, ArH), 7.45 (d, J=2.2 Hz, 2H, ArH), 8.32 (d, J=2.2 Hz, 2H, ArH), 8.86 (d, H=10.3 Hz, 2H, ArH), FT-IR ($cm^{-1}$) KBr: 3434, 3119, 2957, 2797, 1726, 1572, 1415, 1284, 1153, 1113, 642. Anal. Calcd. for $C_{34}H_{39}N_4O_{12}S_2 \cdot 2$ HCl·0.5 $H_2O$; C, 48.57; H, 4.91; N, 6.66; S, 7.63; Cl, 8.43; Found: C, 48.45; H, 4.93; N, 6.84; S, 7.75; Cl, 8.55.

Other compounds of the invention can be prepared according to the method in Example 2 by substituting a polyamine such as spermidine or N-methyl-N,N-dipropyl amine for spermine and reacting the polyamine with 8-methoxypsoralen sulfonyl chloride. Also see Scheme I. Table 1 illustrates moieties comprising furocoumarin-sulfonamide derivatives. The moieties are deignated by R and A. Column headings labeled m and n indicate the number of the pentultimate and ultimate $CH_2$ moieties respectively. The approximate melting point of a compound in degrees centigrade is indicated in the column labelled mp(° C.). Each compound is designated by a numeral in the column labelled "Compound Number." These numeric designations are to provide clarity to the table hereinafter and in no way limit the designation or description of the compounds, or the scope of the invention.

TABLE 1

| Compound Number | R1 | R2 | R3 | A | m | n | mp (°C.) |
|---|---|---|---|---|---|---|---|
| 1) | H | H | H | $NH(CH_2)_4NH$ | 3 | 3 | 278–280 |
| 2) | H | B | H | $NH(CH_2)_4NH$ | 3 | 3 | 207–208 |
| 3) | H | B | H | NH | 4 | 3 | 227–229 |
| 4) | H | B | H | $NCH_3$ | 3 | 3 | 198–199 |
| 5) | H | B | H | NH | 3 | 3 | 228–229 |
| 6) | H | B | H | $NH(CH_2)_2NH$ | 3 | 3 | |
| 7) | $CH_3$ | B | $CH_3$ | $NH(CH_2)_6NH$ | 6 | 6 | |
| 8) | $C_2H_5$ | $CH_3$ | $C_2H_5$ | $NC_2H_5$ | 5 | 5 | |

B is the moiety

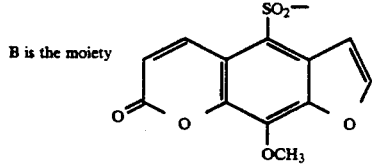

EXAMPLE 3

Protein Kinase C Inhibition

The protein kinase C (PKC) assay is designed to duplicate the in vivo conditions required for protein kinase C function. Therefore, pH, salt and cofactor concentrations are similar to physiologic levels. A lysine rich histone H1 is used in the assay as the phosphorylation acceptor protein because it is readily available and serves as a good substrate for protein kinase C. Enzyme is prepared from rat brain and is purified to apparent homogeneity as determined by a single band on silver stained sodium dodeceyl sulfate (SDS)-polyacrylamide.

In the screening assay, phosphatidylserine (PS) and diacylglycerol (DAG) are co-sonicated to form unilamellar and multilamellar vesicles. The concentrations of lipids in the assay are suboptimal to maximize the detection potential for inhibitors. Potential inhibitor compounds are added to the assay in dimethylsulfoxide (DMSO) at three concentrations to give final inhibitor concentrations of 4.3, 43 and 218 μm, respectively. The assay is started with the addition of enzyme and stopped after 10 minutes by the addition of a 25% trichloroacetic acid (TCA) solution and 1.0 mg/ml bovine serum albumin (BSA). The radioactive histone product is retained and washed on glass fiber filters that allow the unreacted $^{32}$P-ATP to pass through. The amount of phosphorylation is determined by the radioactivity as measured in a scintillation counter. Controls are included in every assay to measure: background activity in the absence of enzyme, activity in the absence of lipids, and the maximum enzyme activity with saturating levels of the activator lipids. Table 2 shows the protein kinase C assay components and their concentrations.

TABLE 2

| Assay Component | Concentration |
|---|---|
| HEPES pH 7.5 | 20 μM |
| $MgCl_2$ | 20 μM |
| $CaCl_2$ | 100 μM |
| EGTA | 95 μM |
| Histone H1 | 200 μg/ml |
| Phosphatidylserine | 40 μg/ml |
| Diacylglycerol | 1.8 μg/ml |
| Protein Kinase C | 0.6 μg/ml |
| $\gamma$-$^{32}$P-ATP | 20 μM |

HEPES is N-[2-hydroxyethyl] piperazine-N'-[2-ethanesulfonic acid] and EGTA is Ethylene-bis(oxyethylenenitrilo) tetraacetic acid.

Protein kinase C assay results are shown in Table 3 in the column labeled PKC. Results are shown as $IC_{50}$, which is the concentration of test compound needed to inhibit 50% of the protein kinase C activity as compared with levels of protein kinase C activity in controls. Compounds of the invention were able to effectively inhibit protein kinase activity. Table 3 shows that protein kinase C is efficiently inhibited by furo-coumarinsulfonamides at micromolar concentrations. Specifically, Table 3 shows that the furu-coumarinsulfonamide compounds tested inhibit PKC at concentrations ranging between 17 and 30 micromolar. Compound numbers indicate the number of the compound of the invention shown in Table 1. In Table 3, compound numbers correspond to the number of the compound of the invention shown in Table 1.

TABLE 3

| Compound Number | PKC $IC_{50}$ ($\mu M$) |
| --- | --- |
| 1 | 30 |
| 2 | 24 |
| 3 | 21 |
| 4 | 17 |
| 5 | 33 |

EXAMPLE 4 cAMP Dependent Protein Kinase (PKA) Assay

Compounds found to be inhibitors of protein kinase C activity are tested for inhibitory activity against protein kinase (PKA). This enzyme, like protein kinase C, plays an important role in cell-cell communication and is activated by a second messenger, cAMP. Secondary screening against PKA is useful for ascertaining the selectivity of the compounds of the invention. A cAMP dependent protein kinase assay utilizes a catalytic subunit of PKA (Sigma Chemical Company, St. Louis, Missouri) that is mixed with buffer before addition of the inhibitor in dimethylsulfoxide (DMSO). The assay is started by the addition of $^{32}P$-ATP and the reaction is allowed to proceed for 10 min before stopping with 25% trichloroacetic acid (TCA) and 1.0 mg/ml bovine serum albumin (BSA). The phosphorylated protein is isolated by filtration and the radioactivity is counted in a beta scintillation counter. Standard assay components and the concentrations used in a cAMP dependent kinase assay are given in Table 4.

PKA assay results are shown in Table 5 in the column labeled PKA. As shown in Table 5, the compounds of the invention that were tested had no effect on PKA. The tested compounds of the invention are selective for protein kinase C, and have no effect on cAMP dependent protein kinase. This is seen by a comparison of Tables 3 and 5. Table 3 shows that protein kinase C is inhibited by furo-coumarinsulfonamide compounds of the invention in concentrations lower than those which are effective to inhibit protein kinase, i.e PKA, as seen in Table 5. As shown in Table 3, compound 1 had an $IC_{50}$ of 30 $\mu M$ for protein kinase C, whereas in Table 5 compound 1 shows an $IC_{50}$ of >218 $\mu M$ for protein kinase. Thus, the compounds of the invention should have minimal or no effect on the metabolic pathways associated with stimulation of protein kinase by cAMP. In Table 4, compound numbers correspond to the number of the compound of the invention shown in Table 1.

TABLE 4

| Assay Components | Concentration |
| --- | --- |
| HEPES pH 7.5 | 20 $\mu M$ |
| Histone H1 | 200 $\mu g/ml$ |
| Dithiothreitol | 32 $\mu g/ml$ |
| Protein Kinase A | 2.6 $\mu g/ml$ |
| $\gamma$-$^{32}$-32-ATP | 20 $\mu M$ |

TABLE 5

| Compound Number | PKA $IC_{50}$ ($\mu M$) |
| --- | --- |
| 1 | >218 |
| 2 | >218 |
| 3 | >218 |
| 4 | >218 |

EXAMPLE 5

Human Tumor Cell Growth Inhibition

MCF-7 a human breast tumor cell line and MCF-7/ADR an adriamycin resistant line of MCF-7 cells were obtained from the National Cancer Institute, Frederick, Md. CEM cells (ATCC accession number CCL 119) were obtained from the American Type Culture Collection, Rockville, Md.

Human tumor cells are trypsinized (0.05% trypsin, GIBCO), counted with a hemacytometer and seeded at a concentration of 10,000 cells/well in a 96 well microtiter plate. After allowing cells to attach to the surface overnight, the culture medium is aspirated and replaced with 100 $\mu l$ of fresh medium. Test agents are diluted to determine dose response at 2X final concentration and added in quadruplicate at 100 $\mu l$/well to bring the total volume of each well to 200 $\mu l$. The microtiter plate is then incubated at 3 37° C. 5% $CO_2$ overnight (18–24 hrs) before $^3H$-thymidine is added at a concentration of 0.5 $\mu Ci$/well in 50 $\mu l$ culture medium. The plate is incubated again for 4 hrs under the same conditions as above. Supernatant is then aspirated and 50 $\mu l$ trypsin (0.05%, GIBCO) is added to each well. Cells are checked microscopically to determine detachment from surfaces, and plates are then harvested with a cell harvester (PHD, Cambridge Technology, Inc.) Filter papers corresponding to wells are placed in scintillation vials and counted to determine the amount of $^3H$-thymidine incorporated by the cells. Test agent response is compared to a positive control of cell wells with culture media only to determine the $IC_{50}$ $IC_{50}$ is the concentration of test compound required to inhibit fifty percent of the incorporation of $^3H$-thymidine into proliferating cells not exposed to test agent. Uptake of $^3H$-thymidine is a standard test for measuring the metabolism of cells. Cells which are actively proliferating take up $^3H$-thymidine, whereas cells that are not proliferating take up 3H-thymidine at much slower rates or not at all. Test agents that inhibit the uptake of $^3H$-thymidine thus slow the growth of cells.

As shown in Table 6, compounds of the invention were able to inhibit $^3H$-thymidine uptake and thus inhibit the proliferation of the tested cell lines.

TABLE 6

| Compound Number | MCF-7 ($\mu M$) |
| --- | --- |
| 1 | • |

TABLE 6-continued

| Compound Number | MCF-7 (μM) |
| --- | --- |
| 2 | * |
| 3 | 5.5 |
| 4 | 11 |

*indicates that the compound was too insoluble to test

EXAMPLE 6

Human Keratinocyte Inhibition

Proliferating keratinocytes (NHEK cells purchased from Clonetics, Inc., San Diego, Calif.) in second passage were grown in Keratinocyte Growth Medium (KGM) (Clonetics, Inc.) Cells are trypsinized (0.025% trypsin, Clonetics), counted with a hemacytometer (Scientific Products), and seeded at a concentration of 2,500 cells/well in a 96 well microtiter plate. After allowing cells to attach to the surface overnight, the culture medium is aspirated and replaced with 100 K1 of fresh KGM. Test agents are evaluated and $IC_{50}$,s are $^3H$-thymidine determined according to the $^3H$-thymidine incorporation procedures described as in Example 8. IC50 is the concentration of test compound required to inhibit fifty percent of the incorporation of H-thymidine into proliferating cells not exposed to test agent.

Compounds of the invention shown in Table 7 exhibited inhibitory activity against human keratinocytes and thus were effective in slowing the proliferation of the cells. These results indicate that compounds of the invention are active against human keratinocytes, and will be useful in treating topical inflammatory conditions such as psoriasis and other conditions where hyperproliferation of keratinocytes is a symptom.

TABLE 7

| Compound Number | $IC_{50}$ (μM) |
| --- | --- |
| 1 | 11.9 |
| 2 | 1.4 |
| 3 | 15.4 |
| 4 | 9.5 |

EXAMPLE 7

Neutrophil Superoxide Anion ($O_2$-) Release Assay

Neutrophils are isolated form whole blood collected from human volunteers. All reagent materials are obtained from Sigma Chemical Company with the exception of isotonic saline (Travenol Laboratories, Inc., Deerfield, Ill.) and lymphocyte separation medium (Organon Teknika, Durham, N.C.).

Neutrophil Isolation

Whole blood is drawn and mixed with sodium heparin (final conc. 10 units/ml) to prevent clotting. An equal volume of dextran (3.0%) in isotonic saline is added, mixed, and allowed to settle for 30 min to bind red blood cells (RBC). Supernatant is removed, underlayered with lymphocyte separation medium and centrifuged for 40 min at 400 xg in a centrifuge (Beckman GPR, Norcross, Ga.). The pellet is alternately resuspended in 0.2% and 1.6% NaCl to lyse RBCs before washing with Hank's Balanced Salt Solution (HBSS). The washed pellet is resuspended in 10 ml HBSS and placed on ice before counting on a hemacytometer.

Assay Procedure

The neutrophil cell concentration is adjusted to $2 \times 10^6$ cells/ml with HBSS before adding 0.8 ml cells to $12 \times 75$ mm polypropylene test tubes (Fisher Scientific). Test agents are diluted to determine dose response and added at 10X final concentration at a volume of 0.1 ml/tube in duplicate. Then 10X concentrations of cytochrome C (15 mg/ml) with catalase (3000 units/ml) either alone or containing 25 ng/ml phorbol 12-myristate 13-acetate (PMA) are added at a volume of 0.1 ml/tube and incubated at 37° C. for 30 min before stopping the reaction by placing tubes on ice. Tubes are then centrifuged at 900 xg for 10 min, 0.5 ml supernatant is removed and added to 0.5 ml $H_2O$ in a microcuvette. Optical density (OD) of cytochrome c is read in a spectrophotometer (Shimadzu) at 550 nm. The $\Delta OD$ of cytochrome c is obtained between PMA-stimulated and non-stimulated tubes, and the dose responses of the test agents are compared to the positive controls (which contain HBSS in place of test agents). PMA stimulates $O_2$ production which reduces cytochrome c. Reducing cytochrome c increases its absorbance, and the change in OD of cytochrome c is proportional to the amount of $O_2$ produced by PMA stimulation. Inhibition of the $O_2$-burst by test compounds of the invention is seen as a reduction in the change in optical density. Inhibition is expressed as $IC_{50}$ μM and is the amount of test compound that will inhibit fifty percent of the PMA-stimulated respiratory burst, i.e. $O_2$ production.

TABLE 8

| Neutrophil Superoxide Release | |
| --- | --- |
| Compound Number | $IC_{50}$ (μM) |
| 1 | >10 |
| 2 | >10 |
| 3 | >10 |
| 4 | >10 |

We claim:
1. A compound having the formula

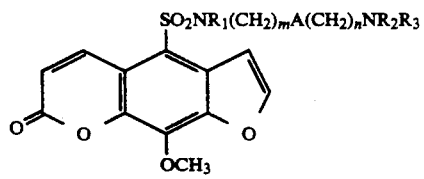

wherein $R_1$, $R_3$, $R_4$, $R_5$ and $R_6$ are independently H or lower alkyl; m, n and p are independently 2, 3, 4, 5 or 6; A is $NR_4(CH_2)_pNR_5$, $NR_6$, O or S; and $R_2$ is independently H, lower alkyl or a moiety of the formula

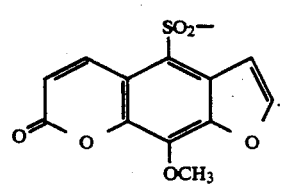

2. The compound of claim 1 wherein $R_1$, $R_3$, $R_4$, $R_5$ and $R_6$ are independently H or lower alkyl; m, n and p are independently 2, 3, 4, 5 or 6; A is $NR_4(CH_2)_pNR_5$ or $NR_6$; and $R_2$ is a moiety of the formula 3. The compound of claim 2 wherein $R_1, R_3, R_4, R_5,$ and $R_6$ are independently H or methyl; m, n and p are independently 3 or 4; A is $NR_4(CH_2)_pNR_5$ or $NR_6$; and $R_2$ is a moiety of the formula

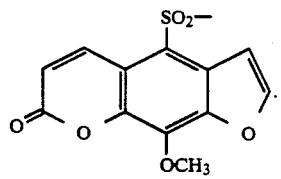

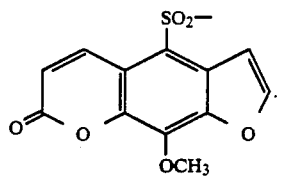

4. A pharmaceutical composition for inhibiting protein kinase C comprising a compound of claim 1 and a pharmaceutically acceptable carrier or diluent.

5. A pharmaceutical composition for inhibiting protein kinase C comprising a compound of claim 2 and a pharmaceutically acceptable carrier or diluent.

6. A pharmaceutical composition for inhibiting protein kinase C comprising a compound of claim 3 and a pharmaceutically acceptable carrier or diluent.

* * * * *

UNITED STATES PATENT AND TRADEMARK OFFICE
CERTIFICATE OF CORRECTION

PATENT NO. : 5,216,014

DATED : June 1, 1993

INVENTOR(S) : Jack B. Jiang and Mary G. Johnson

It is certified that error appears in the above-identified patent and that said Letters Patent is hereby corrected as shown below:

In Column 1, line 56, before 13620, change "266:" to --262:--

In Column 5, line 8, after PMA, change "in vitro" to -- *in vitro* --

In Column 5, line 14, after of, change "c-myc, c-fos" to -- *c-myc, c-fos* --

In Column 5, line 15, before nuclear, change "c-cis, c-fms" to -- *c-cis, c-fms* --

In Column 6, line 32, after to, change "i)" to -- 1) --

In Column 9, line 6, after -sulfonamide], change "(2)" to -- (*2*) --

In Column 9, line 9, after proyl], change "-s-methyl to -- -8-methoxy --

In Column 9, line 10, change "(1)" to -- (*1*) --

In Column 9, line 18, after compound, change "1" to -- *1* --

In Column 9, line 29, before Elemental, change "Cm$^{-1}$" to -- cm$^{-1}$ --

In Column 9, line 35, after compound, change "2" to -- *2* --

In Column 10, line 24, after the, change "in vivo" to -- *in vivo* --

UNITED STATES PATENT AND TRADEMARK OFFICE
CERTIFICATE OF CORRECTION

PATENT NO. : 5,216,014
DATED : June 1, 1993
INVENTOR(S) : Jack B. Jiang, et. al.

It is certified that error appears in the above-indentified patent and that said Letters Patent is hereby corrected as shown below:

In Column 12, line 51, after the , change "$IC_{50}IC_{50}$" to --$IC_{50}.IC_{50}$--.

Signed and Sealed this

Twenty-sixth Day of April, 1994

*Attest:*

BRUCE LEHMAN

*Attesting Officer*   *Commissioner of Patents and Trademarks*